US012702239B2

(12) United States Patent
Bennett et al.

(10) Patent No.: US 12,702,239 B2
(45) Date of Patent: Aug. 11, 2026

(54) SLEEP SEQUENCE INITIATION FOR A SMART BED

(71) Applicant: Purple Innovation, LLC, Lehi, UT (US)

(72) Inventors: Thomas Andrew Bennett, Irvine, CA (US); James Grutta, Draper, UT (US)

(73) Assignee: Purple Innovation, LLC, Lehi, UT (US)

( * ) Notice: Subject to any disclaimer, the term of this patent is extended or adjusted under 35 U.S.C. 154(b) by 645 days.

(21) Appl. No.: 17/978,119

(22) Filed: Oct. 31, 2022

(65) Prior Publication Data

US 2024/0138584 A1 May 2, 2024

(51) Int. Cl.

| | |
|---|---|
| ***A61B 5/11*** | (2006.01) |
| ***A47C 21/04*** | (2006.01) |
| ***A47C 31/00*** | (2006.01) |
| ***A47C 31/12*** | (2006.01) |
| ***A61B 5/00*** | (2006.01) |
| ***A61B 5/117*** | (2016.01) |
| ***A61M 21/00*** | (2006.01) |
| ***G05B 15/02*** | (2006.01) |
| *A47C 27/08* | (2006.01) |

(52) U.S. Cl.

CPC .......... *A47C 31/123* (2013.01); *A47C 21/042* (2013.01); *A47C 21/048* (2013.01); *A47C 31/008* (2013.01); *A61B 5/1116* (2013.01); *A61B 5/117* (2013.01); *A61B 5/4561* (2013.01); *A61M 21/00* (2013.01); *G05B 15/02* (2013.01); *A47C 27/083* (2013.01); *A61M 2230/62* (2013.01)

(58) Field of Classification Search

CPC ........ A61M 2230/62; A61M 2230/005; A61M 2230/63

USPC .......................................................... 700/302

See application file for complete search history.

(56) References Cited

U.S. PATENT DOCUMENTS

| | | | | |
|---|---|---|---|---|
| 11,213,444 | B2 * | 1/2022 | Masuda | A61B 5/002 |
| 2007/0199154 | A1 * | 8/2007 | Escaross | A61G 7/05769 5/713 |
| 2014/0277778 | A1 * | 9/2014 | Nunn | A47C 27/082 700/282 |
| 2016/0300467 | A1 * | 10/2016 | Warren | G08B 21/02 |
| 2017/0169690 | A1 * | 6/2017 | Pfeiffer | B60N 2/0029 |
| 2017/0236398 | A1 * | 8/2017 | Eddy | A61B 5/6808 340/573.5 |
| 2018/0032997 | A1 * | 2/2018 | Gordon | G06Q 30/0269 |
| 2020/0253384 | A1 * | 8/2020 | Kubota | A47C 19/045 |

(Continued)

OTHER PUBLICATIONS

Hill et al., U.S. Appl. No. 63/295,221, filed (2021).*

*Primary Examiner* — Emilio J Saavedra

(74) *Attorney, Agent, or Firm* — Foley & Lardner LLP

(57) ABSTRACT

A smart bed automatically initiates a sleep sequence upon detecting the presence of an individual in a sleeping position on a sleep surface of the smart bed. Such a smart bed may include a mattress that defines the sleep surface, at least one sensor associated with the sleep surface, and a processor that communicates with the at least one sensor and controls one or more functions of the mattress. Initiation of the sleep sequence may include initiating one or more functions of the smart bed and, optionally, one or more functions of an environment within which the smart bed is located to help the individual relax and fall asleep.

21 Claims, 6 Drawing Sheets

(56) References Cited

U.S. PATENT DOCUMENTS

| | | | | |
|---|---|---|---|---|
| 2021/0153661 | A1 * | 5/2021 | Wei | A47L 15/4295 |
| 2021/0169233 | A1 * | 6/2021 | Tsern | A61B 5/6892 |
| 2021/0204720 | A1 * | 7/2021 | Karschnik | A47C 21/044 |
| 2021/0378415 | A1 * | 12/2021 | Ohno | A61G 7/05776 |
| 2023/0210269 | A1 * | 7/2023 | Hill | A47C 19/022<br>362/130 |
| 2024/0427421 | A1 * | 12/2024 | Tadele | A61B 5/6892 |

* cited by examiner 20
61
60
26
24
23
27
28
10
23
60
61H
64
62
61I
61F 10
23
60
50
24
52
20
22

23
22
23
24
25
20
10
26
40T
27
40E
28
40L
23
50
52

SLEEP SEQUENCE INITIATION FOR A SMART BED

TECHNICAL FIELD

This disclosure relates generally to smart beds that automatically initiate a sleep sequence upon detecting the presence of at least one individual in a sleeping position on a sleep surface thereof. More specifically, this disclosure relates to smart beds that automatically initiate one or more pre-programmed functions upon detecting the presence of an individual in a sleeping position on a sleep surface thereof. This disclosure also relates to methods for using smart beds, include methods that including detecting the presence of an individual on a sleeping position on a sleep surface of the smart bed and initiating one or more functions of the smart bed in response to detecting the presence of the individual in the sleeping position on the sleep surface.

SUMMARY

In various aspects, sleep sequences for smart beds are disclosed.

A smart bed of this disclosure is equipped to automatically initiate a sleep sequence upon detecting the presence of at least one individual in a sleeping position on a sleep surface of the smart bed. Such a smart bed may include a mattress that defines the sleep surface, at least one sensor associated with the sleep surface, and a processor that communicates with the at least one sensor and controls one or more functions of the mattress. A smart bed may also include a foundation for the mattress. In some embodiments, the smart bed may interact with an environment in which the mattress is located.

The mattress may have any suitable configuration. As a few examples, the mattress may comprise a conventional mattress with coils, a so-called "memory foam" mattress, a mattress with one or more bladders that may be selectively pressurized, a gel mattress, or a mattress that includes a combination of these and/or other features.

The at least one sensor may be capable of detecting motion or another activity (e.g., proximity, the application of pressure, etc.) to a surrounding area of the sleep surface of the mattress. Each sensor may comprise an accelerometer. More specifically, the at least one sensor may be positioned adjacent to the sleep surface at a location where it may detect the presence of an individual on the sleep surface, and even detect whether the individual is laying on the sleep surface in a sleeping position. In some embodiments, the at least one sensor may be positioned at a location where an individual would be expected to rest their body, or torso, and/or their legs when laying in a sleeping position on the sleep surface. In other embodiments, the at least one sensor may comprise a group of sensors, such as any combination of a sensor at the side of the mattress (e.g., a sensor positioned over a rail of the mattress, on a side of a rail of the mattress, within a rail of the mattress, etc.), a sensor at a location where an individual would be expected to rest their body when assuming a sleeping position on the sleep surface, a sensor at a location where the individual would be expected to rest their legs when assuming a sleeping position on the sleep surface, and a sensor at any other location that may enable it detect activities that are ordinarily associated with an individual "climbing into bed" (e.g., sitting or otherwise moving on a side of the mattress or on the mattress, moving toward a center of the mattress, and extending their legs, etc.).

The processor that communicates with (e.g., receives signals from, etc.) each sensor associated with the sleep surface of the mattress may comprise one or more processing elements of a suitable type. In some embodiments, the processor may comprise one or more microcontrollers, which may execute an embedded program (e.g., firmware) to control one or more dedicated functions. The processor may be carried by the mattress (e.g., internally, adjacent to a foot of the mattress; etc.).

Based on data generated by the at least one sensor, the processor may be programmed to detect a presence of an individual on the sleep surface of the mattress. Based on data generated by the at least one sensor, the processor may also be programmed to determine a location of the individual on the sleep surface. Based on data generated by the at least one sensor, the processor may be programmed to determine an orientation of the individual on the sleep surface (e.g., whether the individual is in an inclined position, or a sitting position, on the sleep surface; whether the individual is in a reclined position, or a sleeping position, on the sleep surface; etc.). Programming of the processor may even enable it to identify the individual who is present on the sleep surface; a processor programmed in this manner may initiate the at least one function in a manner that corresponds to an identity of the individual present on the sleep surface.

In some embodiments, a determination of whether an individual has assumed a sleeping position on a sleep surface of a mattress may be based simply on determination of a position of the individual from the plurality of sensors, movement or other activity (e.g., the proximity of the subject to a sensor, the application of pressure, etc.) by the individual to a location of the sleep surface, where an individual would be expected to place one or more body parts (e.g., their legs, their body, their head, etc.) as they lay in a sleeping position on the sleep surface.

In other embodiments, a determination that an individual is likely to have assumed a sleeping position on the sleep surface of the mattress may be additionally based on the individual's movement onto or on the sleep surface of the mattress or other activity (e.g., movement into proximity to a sensor, the application of pressure to a sensor, etc.) at location(s) where the individual would be expected to place one or more body parts (e.g., their legs, their body, their head, etc.) as they assume a resting position or sleeping position on the sleep surface. The detection of such movement or another activity, or the lack of movement or another activity, may provide an indication of the approximate location, position, or state of the individual on the relevant portion of the sleep surface by an individual who typically uses the mattress, by any individual, etc., as opposed to movement of or the presence of something else (e.g., a pet, an object, etc.) onto or on the relevant portion of the sleep surface.

In still other embodiments, a determination that an individual is likely to have assumed a sleeping position on the sleep surface of the mattress may be based on a sequence of events detected by a group of sensors associated with the sleep surface of the mattress. The sequence of events may comprise a sequence of events that ordinarily occurs when an individual "climbs into bed" or a sequence of events that occurs as a particular individual (e.g., an individual who typically uses the smart bed, etc.) assumes a sleeping position on the sleep surface. For example, a sensor at an edge of the mattress (e.g., a sensor positioned over a rail of the mattress, on a side of a rail of the mattress, within a rail of the mattress, etc.) may detect an individual sitting or otherwise positioning themselves on an edge of the bed.

Then a sensor at a location where an individual would be expected to rest their body and/or a sensor at a location where the individual would be expected to rest their legs may detect the individual assuming a resting or sleeping position on the sleep surface. Alternatively or additionally, after detecting the presence of the individual on the side of the bed, one or more sensors may detect other activity associated with climbing into bed, such as movement of the individual from the edge of the sleep surface towards a center of the sleep surface, which may include sensing the movement of an individual based on the movement relative to the sensor, sensing movement in a manner that resembles extension of an individual's legs, and the like.

The processor may be programmed to distinguish a sequence of events indicative of an individual assuming a sleeping position on the sleep surface from other events, such as an individual merely sitting on the sleep surface, an individual moving over the sleep surface (e.g., a person crawling over the sleep surface, a child bouncing on the mattress, etc.), an animal on the sleep surface, an object placed on the sleep surface, etc.

Once the processor determines that an individual has likely assumed a sleeping position on the sleep surface of the mattress, the processor may initiate a sleep sequence. Initiation of the sleep sequence may include automatically activating one or more functions of the mattress, the smart bed, and/or an environment in which the smart bed is located. A few nonlimiting examples of functions that may be activated as part of a sleep sequence include adjusting an orientation of the mattress or a portion thereof, adjusting a firmness (or softness) of the mattress or a portion thereof (e.g., pressurization of a bladder within the mattress, etc.), ventilating the mattress or a portion thereof, adjusting a temperature of the mattress or a portion thereof, actuating an anti-snore feature of the smart bed (e.g., its foundation, its mattress, etc.), dimming of lights or turning off lights in a room where the smart bed is located (e.g., a bedroom) and, optionally, elsewhere in the living space (i.e., outside the room where the smart bed is located), etc.

In addition to the mattress, the at least one sensor, and the processor, a smart bed of this disclosure may include a transceiver, along with an associated antenna. The transceiver may be associated with the processor in a manner that enables the processor to communicate with a processor of a portable electronic device (e.g., a smart phone, a tablet computer, a smart watch, etc.). The processor of the portable electronic device may execute a smart bed control app, which may enable an individual to use the portable electronic device to control operation of the smart bed and/or devices in the environment in which the smart bed is located. The smart bed control app may initiate communication between the processor of the portable electronic device and the processor of the smart bed. Alternatively, the processor of the smart bed may be programmed to wake the portable electronic device as the smart bed (e.g., a sensor, etc., of the smart bed) detects the presence of the portable electronic device or the individual in close proximity to the mattress and/or detects the presence of an individual on the sleep surface of the mattress. The processor of the smart bed may then communicate with the processor of the portable electronic device in a manner that causes the processor of the portable electronic device to initiate execution of the smart bed control app.

In embodiments where the smart bed includes a foundation, the foundation may comprise an adjustable platform. The adjustable platform may include a plurality of support surfaces, at least one motor, and a processor. The plurality of support surfaces can carry the mattress of the smart bed. The at least one motor, under control of the processor, may move the plurality of support surfaces to desired orientations, which may move a mattress carried by the plurality of support surfaces to a desired arrangement. In addition, the adjustable platform may include a transceiver, along with an associated antenna. The transceiver may establish communication with the processor of the remainder of the smart bed (e.g., a processor carried by the mattress, etc.) and/or with a processor of a portable electronic device, such as a smart phone, a tablet computer, or a smart watch, which may execute the smart bed control app. Such an arrangement may enable the smart bed control app to place the adjustable platform and a mattress carried by the adjustable platform into a desired sleeping arrangement when an individual assumes a sleeping position on the mattress.

In a method of this disclosure, a smart bed initiates a sleep sequence. Such a method may include detecting a presence of an individual on a sleep surface of a mattress of the smart bed, determining a location of the individual on the sleep surface, and initiating at least one function of the smart bed based on the location of the individual on the sleep surface.

Additionally, such a method may include determining an orientation of the individual on the sleep surface. Determining the orientation of the individual on the sleep surface may include determining an orientation of the individual across at least a portion of the sleep surface and/or determining whether the individual is in a sitting position on the sleep surface or in a sleeping position on the sleep surface.

In some embodiments, in addition to detecting the presence of an individual on the sleep surface and determining the location of the individual on the sleep surface, the method may include identifying the individual present on the sleep surface. In such embodiments, initiating the at least one function may comprise initiating the at least one function in a manner that corresponds to the identity of the individual present on the sleep surface.

Such a method may include establishing communication between a processor of the smart bed and a portable electronic device (e.g., a smart phone, a tablet computer, a smart watch, etc.), which may execute a smart bed control app. In embodiments where the method also includes identifying the individual present on the sleep surface, communication may be established between the processor of the smart bed and the portable electronic device of the individual present on the sleep surface. Communication between the processor of the smart bed and the portable electronic device may occur automatically upon detecting the presence of the individual on the sleep surface, for example, in a sleeping position on the sleep surface. The app may enable an individual to terminate the sleep sequence, to select one or more functions to be executed as part of the sleep sequence, or to adjust one or more functions of a preprogrammed sleep sequence.

The sleep sequence may include initiating one or more functions of the smart bed, its mattress, or the sleep surface of the mattress. Such functions may include, but are not limited to, heating and/or cooling the sleep surface to a pre-set temperature, ventilating at least a portion of the sleep surface, providing the mattress with a pre-set firmness, turning on an anti-snore feature of the smart bed (e.g., of its foundation, its mattress, etc.), adjusting an orientation of at least a portion of the mattress, and turning on and/or off lighting features. Other functions of a smart bed may also be initiated.

In addition to initiating one or more functions of the smart bed, at least one function may be initiated in an environment in which the smart bed is located. Such a function may include adjusting lighting within the environment (e.g., dimming or shutting off room lighting, turning a reading light and/or nightlight on, etc.), closing window blinds or shutters, adjusting a temperature within the environment, playing audio (e.g., music, audiobooks, sounds conducive to rest and/or sleep, subliminal sessions to be played during sleep, white noise, etc.), initiating an alarm system of a building or unit in which the smart bed is located, determining and adjusting, as necessary, the status of any of various systems and/or devices (heating/air conditioning, lighting, media, appliances, garage doors, etc.) of the building or unit where the smart bed is located, and the like.

Other aspects of the disclosed subject matter, as well as features and advantages of various aspects of the disclosed subject matter, should be apparent to those of ordinary skill in the art through consideration of the ensuing description, the accompanying drawings, and the appended claims.

DETAILED DESCRIPTION

Figure 1:
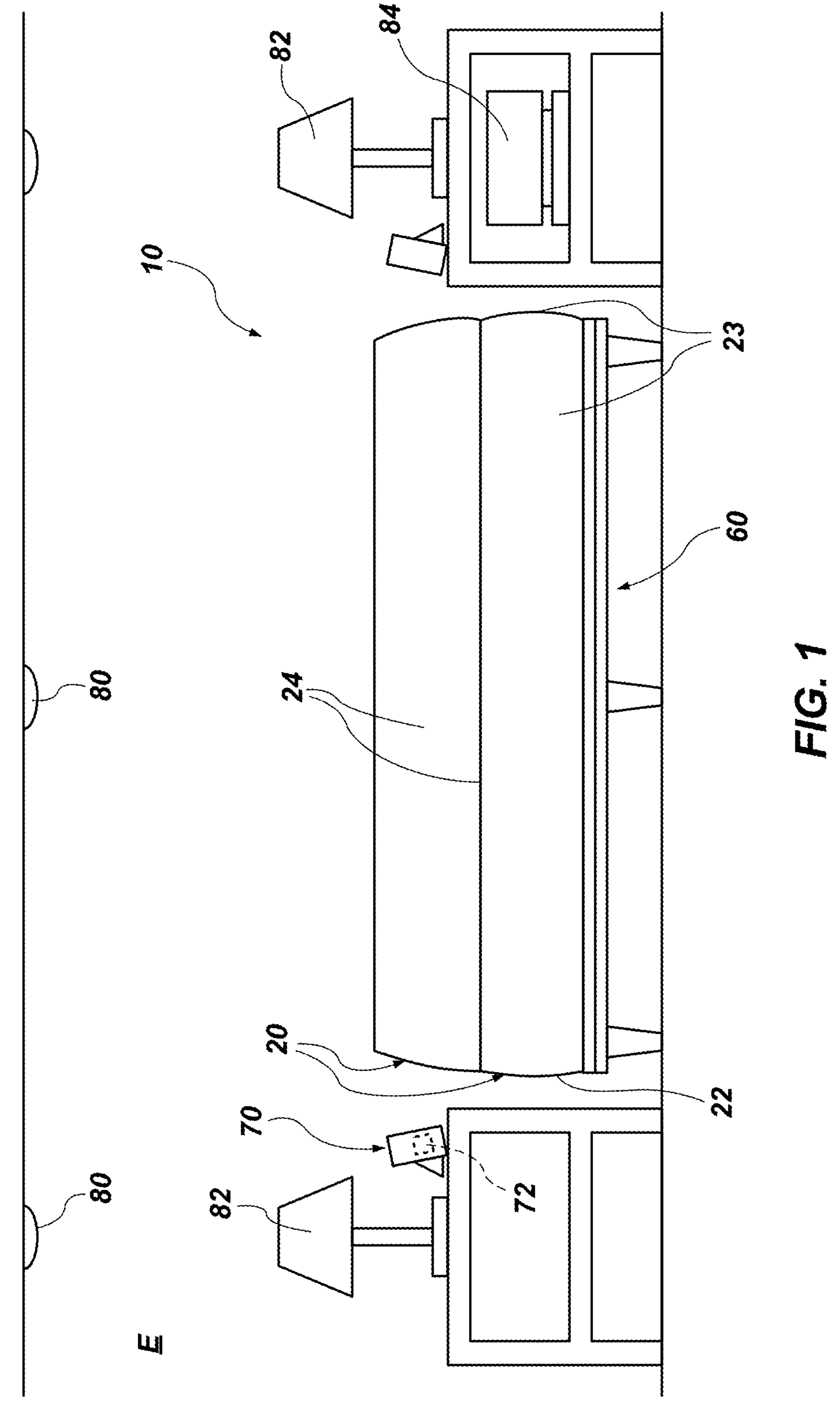
FIG. 1 provides a representation of an embodiment of a smart bed according to this disclosure and an environment (e.g., a bedroom, etc.) in which the smart bed is located.
Figures 2, 3, 4:
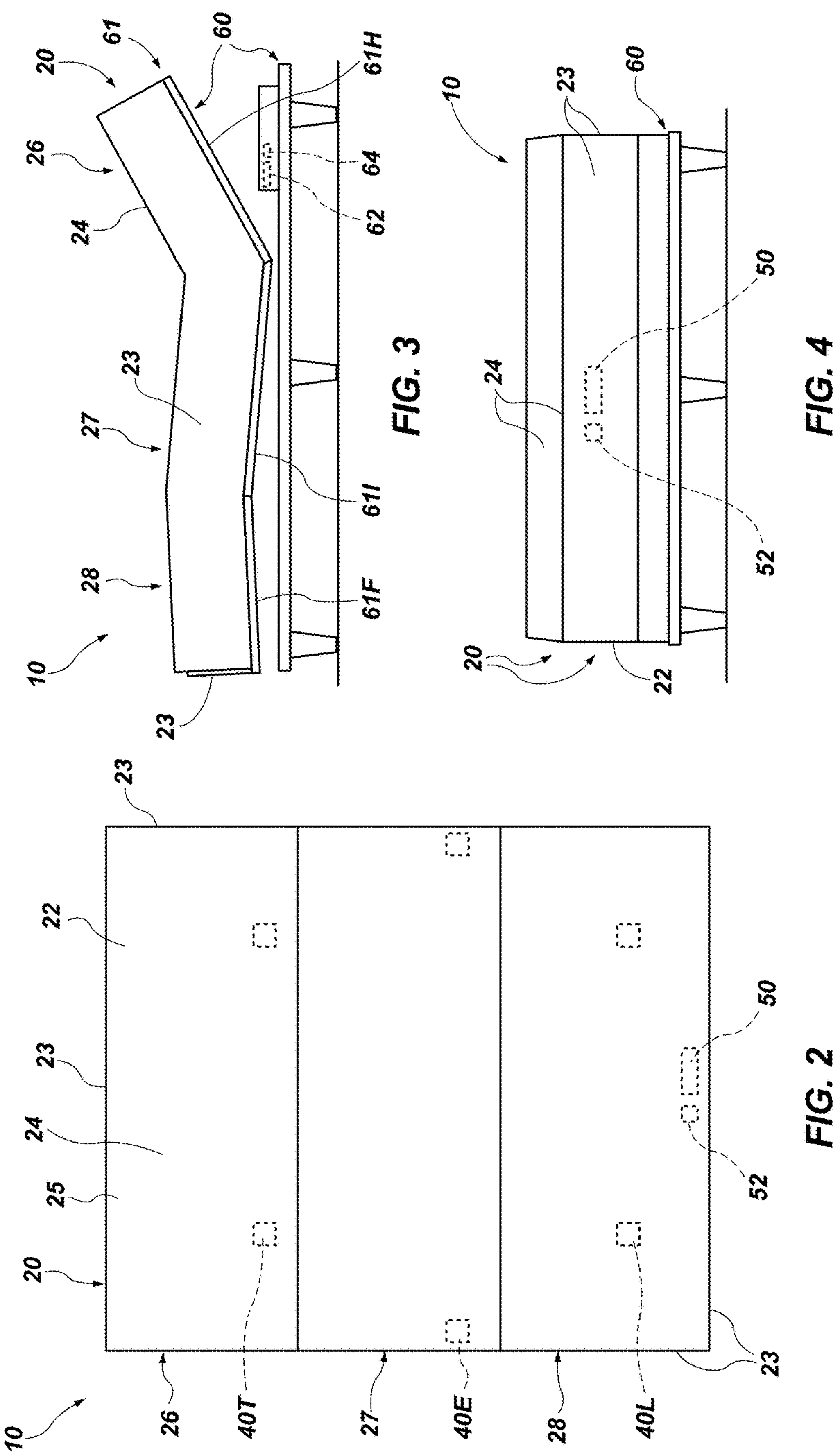
FIG. 2 provides a top view of the embodiment of the smart bed shown in FIG. 1.
FIG. 3 is a side view of the embodiment of the smart bed shown in FIG. 1.
FIG. 4 is a foot end view of the embodiment of the smart bed shown in FIG. 1.

FIGS. 1-4 illustrate an embodiment of a smart bed 10. The smart bed 10 includes a mattress 20, at least one sensor 40 (including, without limitation, one or more thoracic sensors 40T, one or more leg sensors 40L, and/or one or more ambient environment sensors 40E, etc.), a processor 50, and at least one transceiver 52 with an associated antenna (not shown). In addition, the smart bed 10 may include a foundation 60.

The mattress 20 of the smart bed 10 may have any suitable shape and dimensions and may include a cover 22 that contains various internal elements (not shown) of the mattress 20. The mattress may include edges 23, a top surface, or sleep surface 24, between top ends of the edges 23, and a bottom surface, or base 29, between bottom edges of the edges 23. The sleep surface 24 of the mattress 20 may be configured to be slept on by at least one individual. The sleep surface 24 may include edges 25 at locations adjacent to side edges 23 of the mattress 20, a head portion 26, an intermediate portion 27, and a foot portion 28.

The mattress 20 may comprise any suitable type of mattress, such as a conventional mattress with springs and foam, a foam mattress, a memory foam mattress, a mattress with pressurizable bladders (e.g., air chambers, etc.), a mattress that includes a gel grid (e.g., those available from Purple Innovation, LLC, of Lehi, Utah and disclosed by U.S. Pat. Nos. 7,060,213, 7,076,822, and 8,919,750, which may be formed from any suitable material, including, but not limited to, an extended A-B-A triblock copolymer, such as those disclosed by U.S. Pat. Nos. 6,413,458, 6,797,765 and 7,964,664; the entire disclosures of each of the foregoing patents are hereby incorporated herein), or a mattress that includes any combination of these and/or other features.

The one or more sensors 40 may be carried by the mattress 20. Without limitation, at least one sensor 40 may be positioned adjacent to the sleep surface 24 of the mattress 20. For example, a sensor 40 may be positioned within a cover 22 of the mattress 20 in a manner that enables the sensor 40 to detect activity occurring on a sleep surface 24 of the mattress 20. More specifically, each sensor 40 may be positioned within a recess or a receptacle that opens to and communicates with an outer surface of a component of the mattress 20 that carries the sensor 40, with the cover 22 being placed over the recess or receptacle. In other embodiments, the sensor 40 may be incorporated into the cover 22 or positioned between the cover 22 and internal components (not shown) (e.g., a top layer of foam, gel, etc.) of the mattress 20.

In some embodiments, the mattress 20 may carry a plurality of sensors 40. Without limitation, at least one thoracic sensor 40T may be positioned at the head portion 26 and/or the intermediate portion 27 of the mattress 20. At least one leg sensor 40L may be positioned at the foot portion 28 of the mattress 20. At least one ambient environment sensor 40E may be positioned at an edge 23 (e.g., on, adjacent to, or within a rail, etc.) of the mattress 20. In a specific embodiment, the mattress 20 may comprise a gel grid, with each thoracic sensor 40T and leg sensor 40L being positioned within a hollow column of the gel grid, adjacent to an upper surface of the gel grid, and each ambient environment sensor 40E being positioned within a recess or cavity that opens to or otherwise communicates with an outer surface of a side rail of the mattress 20.

The at least one thoracic sensor 40T may facilitate detection of the presence (or absence) of an individual on the sleep surface 24 of the mattress 20. In addition, the at least one thoracic sensor 40T may be used to monitor one or more of the individual's movement (e.g., motion, position on the sleep surface 24, etc.), respiration, and heart rate. The at least one thoracic sensor 40T may also monitor the temperature of the individual's body and, optionally, humidity. In a specific embodiment, the at least one thoracic sensor 40T may include an inclinometer (e.g., an inclinometer available from STMicroelectronics of Plan-les-Ouates, Switzerland, etc.), an accelerometer (e.g., an accelerometer available from MEMSIC Inc. of Andover, Massachusetts, etc.), and a plurality of temperature/humidity sensors (e.g., a temperature and/or humidity sensor available from Sensiron AG of Stäfa, Switzerland, etc.).

The at least one leg sensor 40L may facilitate the detection of the presence (or absence) of an individual on the sleep surface 24 of the mattress 20. In addition, the at least one leg sensor 40L may be used to monitor the individual's movement (e.g., motion, position, etc.), respiration, and heart rate. The at least one leg sensor 40L may monitor the temperature of the individual's legs and, optionally, humidity. In a specific embodiment, the at least one leg sensor 40L may include an accelerometer (e.g., an accelerometer available from MEMSIC Inc. of Andover, Massachusetts, etc.) and a plurality of temperature/humidity sensors (e.g., a temperature and/or humidity sensor available from Sensiron AG of Stäfa, Switzerland, etc.).

The at least one ambient environment sensor 40E may facilitate the detection of the presence (or absence) of an individual in proximity to a side edge 23 of the mattress 20 or on the sleep surface 24 of the mattress 20. In addition, the at least one ambient environment sensor 40E may be used to monitor information about an environment (e.g., a room, etc.) within which the mattress 20 is located, such as its temperature and/or humidity. In a specific embodiment, the at least one ambient environment sensor 40E may include an accelerometer (e.g., an accelerometer available from MEMSIC Inc. of Andover, Massachusetts, etc.) and a temperature/humidity sensor (e.g., a temperature and/or humidity sensor available from Sensiron AG of Stäfa, Switzerland, etc.).

In the illustrated embodiment of mattress 20, each thoracic sensor 40T and leg sensor 40L is shown at a location where an individual is expected to lie on the sleep surface 24 of the mattress 20 as he or she sleeps, with the mattress 20 having a size that accommodates two individuals. In other embodiments, including small mattresses (e.g., twin size, twin XL (extra long) size, full size, etc.) and large mattresses (e.g., queen size, king sizes, etc.), thoracic sensors 40T and leg sensors 40L may be positioned along a midline of the mattress—alone or in combination with other sensor placements.

The processor 50 may comprise one or more processing elements of a suitable type (e.g., microprocessors, microcontrollers, digital signal processors (DSPs), etc.). In some embodiments, the processor 50 may comprise one or more microcontrollers, which may execute embedded programming (e.g., firmware) to control one or more dedicated functions. The processor 50 may be carried by the mattress 20 of the smart bed 10 (e.g., internally, adjacent to a foot **23*f* of the mattress 20; etc.), the foundation 60 of the smart bed 10**, or elsewhere.

Activity detected by the sensors 40 may be communicated to the processor 50. The processor 50 may execute a program to determine whether the data from the sensors 40 indicates that an individual has assumed a resting position or a sleeping position on the sleep surface 24 of the mattress 20, whether the data from the sensors 40 comprises a sequence of events indicative of an individual getting into bed or climbing into bed to rest or sleep, or the like. If the processor 50 determines that an individual has assumed a resting position or a sleeping position on the sleep surface 24, that a sequence of events has occurred that culminated in the individual assuming a resting position or a sleeping position on the sleep surface 24, or the like, then the processor 50 may execute one or more programs that affect a state of the mattress 20, the smart bed 10 of which the mattress 20 is a part, and/or the environment in which the smart bed 10 is located. Execution of the one or more programs by the processor 50 may be referred to as execution of a "sleep sequence" by the processor 50.

The transceiver 52 may be associated with the processor 50 in a manner that enables the processor 50 to communicate with a processor 72 of a portable electronic device 70 (e.g., a smart phone, a tablet computer, a smart watch, etc.) or another device. Without limitation, the transceiver 52 may comprise one or more of a WiFi transceiver, a Bluetooth® transceiver, a near-field communication (NFC) (e.g., radiofrequency (RF), etc.) transceiver, a 2.4 GHz RF transceiver, or the like, along with its associated antenna. The transceiver 52 may be carried by the mattress 20 of the smart bed 10, by the foundation 60 of the smart bed 10, or elsewhere. In some embodiments, the transceiver 52 may be associated with (e.g., located adjacent to, packaged with, etc.) the processor 50 of the smart bed 10.

The processor 72 of the portable electronic device 70 may execute a smart bed control app, which may enable an individual to use the portable electronic device 70 to control operation of the smart bed 10 and/or devices in the environment E in which the smart bed 10 is located. The smart bed control app may initiate communication between the processor 72 of the portable electronic device 70 and the processor 50 of the smart bed 10. Alternatively, the processor 50 of the smart bed 10 may be programmed to wake the processor 72 of the portable electronic device 70 as a component of the smart bed 10 (e.g., at least one sensor 40, etc.) detects the presence of the portable electronic device 70 or the individual in close proximity to the mattress 20 and/or detects the presence of an individual on the sleep surface 24 of the mattress 20. The processor 50 of the smart bed 10 may then cause the processor 72 of the portable electronic device 70 to initiate execution of the smart bed control app.

The foundation 60 of the smart bed 10 may include any suitable foundation for the mattress 20. In some embodiments, the foundation 60 may comprise an adjustable platform (e.g., the Purple® Ascent Base™ adjustable platform, available from Purple Innovation, LLC, of Lehi, Utah, etc.). Such a foundation 60 may include a processor 62 (e.g., a microcontroller, a microprocessor, etc.), which may control movement of one or more adjustable sections 61H, 61I, 61F of a platform 61 that carries the mattress 20. In addition, such a foundation 60 may include a transceiver 64 (e.g., a WiFi transceiver, a Bluetooth® transceiver, a near-field communication (NFC) (e.g., RF, etc.) transceiver, a 2.4 GHz RF transceiver, etc.), along with an associated antenna (not shown). The transceiver 64 may receive signals from the processor 50 of the mattress 20 and/or a processor 72 of a portable electronic device 70 that may cause the processor 62 of the foundation 60 to move one or more sections 61H, 61I, 61F of the platform 61 of the foundation 60 in a desired manner (e.g., to move the mattress 20 or a portion thereof to a desired orientation, to operate an anti-snore feature of the foundation 60, etc.). In other embodiments, the foundation 60 may comprise a stationary foundation (e.g., a platform style bed frame, a conventional bed frame and box spring, etc.).

Figure 5:
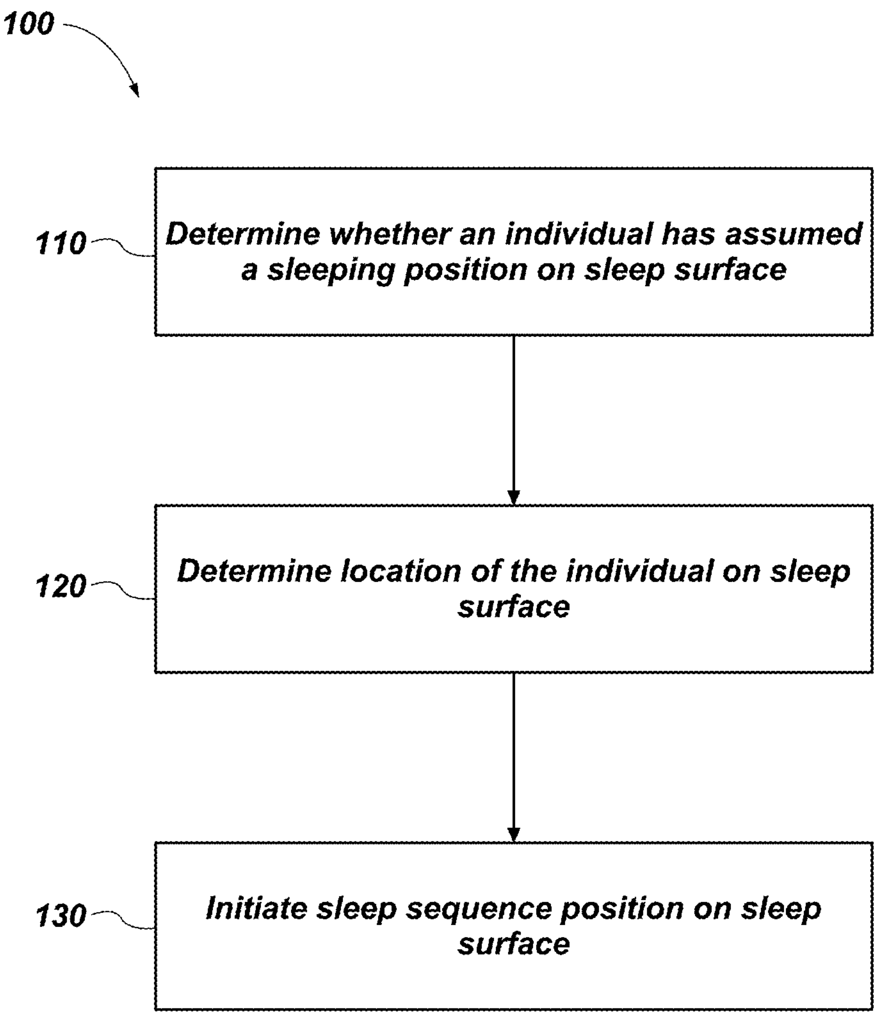
FIG. 5 is a flow diagram illustrating various acts that may occur in an embodiment of a method for initiating a sleep sequence with a smart bed.

FIG. 5 is a diagram illustrating the flow of an embodiment of a method 100 of initiating a sleep sequence on a smart bed 10, such as that depicted by FIGS. 1-4. The method 100 may include determining whether an individual has assumed a resting position or a sleeping position on the sleep surface 24 (FIGS. 1-4) of a mattress 20 (FIGS. 1-4) of the smart bed 10, at reference 110, determining a location of the individual on the sleep surface 24, at reference 120, and initiating at least one function of the smart bed 10 based on the location of the individual on the sleep surface 24, at reference 130.

Figure 6:
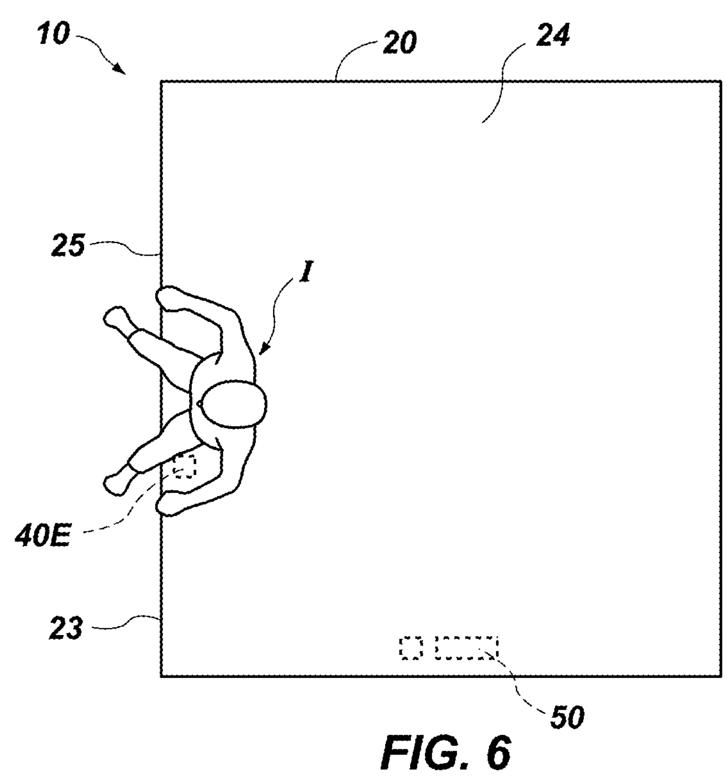
FIGS. 6 and 7 provide top views of the embodiment of the smart bed shown in FIG. 1, illustrating a sequence of events that may occur as an individual assumes a sleeping position on a mattress of the smart bed to cause the smart bed to initiate a sleep sequence.
Figure 7:
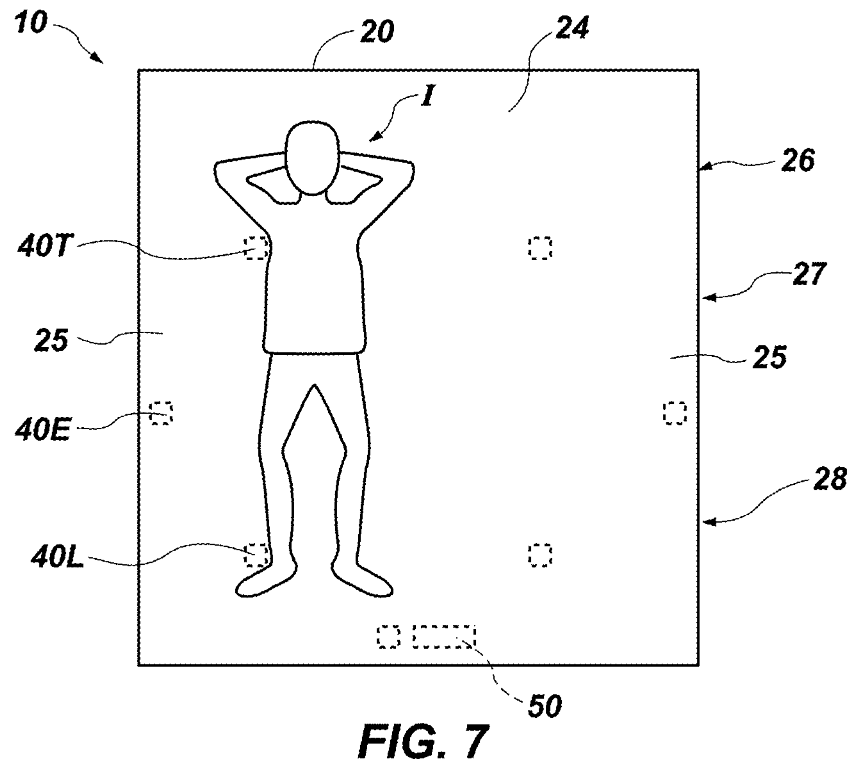

With reference to FIGS. 6 and 7, an embodiment of an event or a sequence of events that may enable the processor 50 to determine that an individual I has assumed a resting position or a sleeping position on the sleep surface 24 of the mattress 20 of the smart bed 10 is illustrated. The event may comprise detection of an individual I in a resting position or a sleeping position on the sleep surface 24. The sequence of events may comprise a sequence of events that ordinarily occurs when an individual I "gets into bed" or "climbs into bed" or a sequence of events that occurs as a particular individual I (e.g., an individual I who typically uses the smart bed, etc.) assumes a resting position or a sleeping position on the sleep surface 24. As illustrated by FIG. 6, an ambient environment sensor 40E at the edge 23 of the mattress 20 may detect an individual I approaching and/or sitting or otherwise positioning themselves on the edge 25 of the sleep surface 24 of the mattress 20. As the ambient environment sensor 40E detects such activity, it may "wake" the processor 50 by communicating data regarding such activity to the processor 50. Then, as shown in FIG. 7, a sensor 40T at a location where an individual I would be expected to rest their body (e.g., the head portion 26 of the mattress 20, the intermediate portion 27 of the mattress 20, etc.) and/or a sensor 40L at a location where the individual I would be expected to rest their legs (e.g., the foot portion 28 of the mattress 20, etc.) may detect the individual I assuming a resting position or sleeping position on the sleep surface 40. Alternatively or additionally, one or more sensors 40E, 40T, 40L may detect other activity associated with climbing into bed, such as movement from the edge 25 of the sleep surface 24 towards a center of the sleep surface 24, movement in a manner that resembles extension of an individual I's legs toward the foot portion 28 of the sleep surface 24, and the like.

Figure 8:
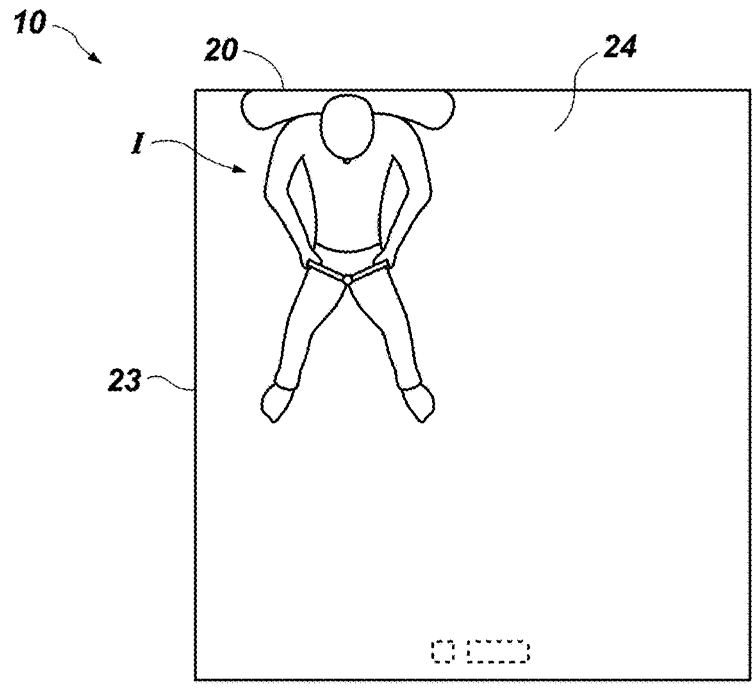
FIGS. 8-10 provide top views of the embodiment of the smart bed shown in FIG. 1, showing various activities that may not cause the smart bed to initiate the sleep sequence.
Figure 9:
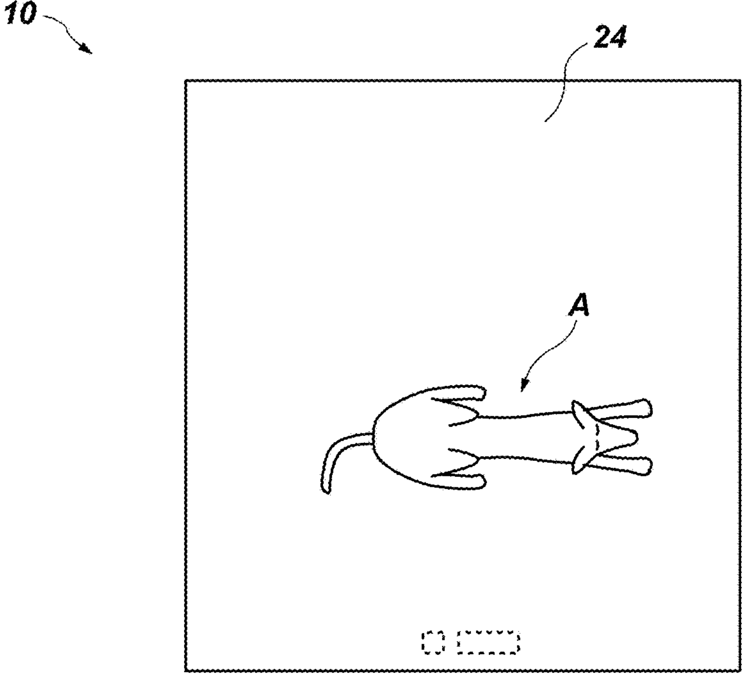
Figure 10:
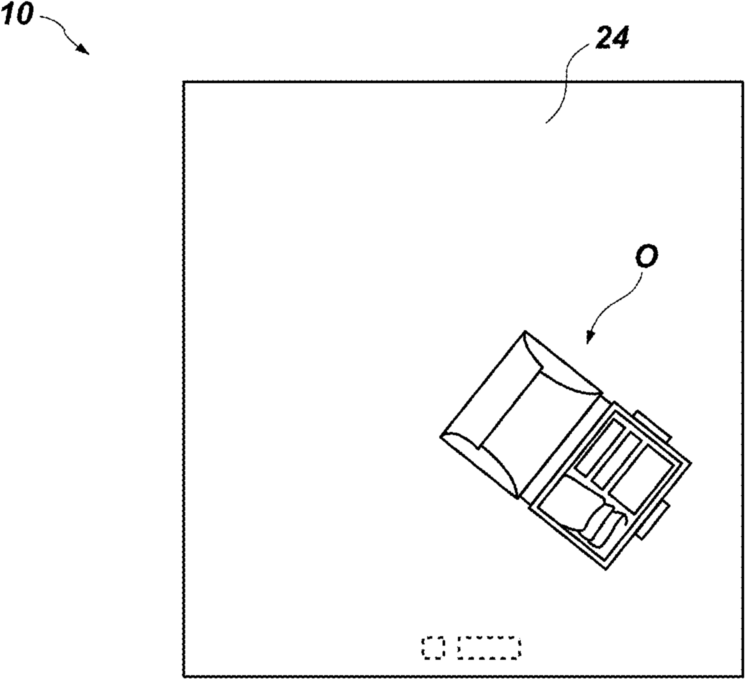

The processor 50 may be programmed to distinguish the presence of an individual on the sleep surface 24 in a resting position or a sleeping position and/or a sequence of events indicative of an individual assuming a sleeping position on the sleep surface 24 from other events. Some examples of such an event include an individual I merely sitting on the sleep surface 24, as shown in FIG. 8, an individual moving over the sleep surface 24 (e.g., a person moving next to, onto, or on the edge 23 or sleep surface 24 of the mattress 20 while making the bed, a person crawling over the sleep surface 24, a child bouncing on the mattress 20, etc. Another example of such an event is an animal A on the sleep surface 24, as shown in FIG. 9. Still another example of such an event includes the presence of an object O (e.g., an object with a weight detectable by one or more sensors 40, such as the depicted suitcase, etc.) on the sleep surface 24, as illustrated by FIG. 10.

With returned reference to FIG. 1, upon determining that an individual has assumed a resting position or a sleeping position on the sleep surface 24 of the mattress 20 of the smart bed 10 (at reference 110 of FIG. 5) and determining a location of the individual on the sleep surface 24 (at reference 120 of FIG. 5), the processor 50 may initiate a sleep sequence. In some embodiments, the processor 50 may communicate with an app of a portable electronic device 70 (e.g., a smart phone, a tablet computer, a smart watch, etc.), which may cause the portable electronic device 70 to alert the individual that the processor 50 is about to initiate a sleep sequence and optionally provide the individual with an opportunity to prevent the processor 50 from initiating the sleep sequence.

Once the processor 50 initiates the sleep sequence, the sleep sequence may affect the mattress 20, the smart bed 10 of which the mattress 20 is a part, and/or the environment E in which the smart bed 10 is located.

The sleep sequence may include initiating at least one function associated with the sleep surface 24 or a portion of the sleep surface 24 on which the individual is located, such as: heating and/or cooling the sleep surface 24 to a pre-set temperature; ventilating at least a portion of the sleep surface 24 (see, e.g., U.S. Pat. No. 11,311,111, the entire disclosure of which is hereby incorporated herein); providing the mattress 20 with a pre-set firmness (see, e.g., U.S. Pat. No. 11,213,139, the entire disclosure of which is hereby incorporated herein); turning on an anti-snore feature of the smart bed 10 (e.g., of its foundation 60, its mattress 20, etc.); adjusting an orientation of at least a portion of the mattress 20 (e.g., with the platform 60, etc.); and turning on and/or off lighting features of the smart bed 10. Other functions of the smart bed 10 may also be initiated.

In addition to initiating one or more functions of the smart bed 10, at least one function in an environment E in which the smart bed 10 is located may be initiated. Such a function may include adjusting lighting within the environment E (e.g., dimming or shutting off room lighting 80, turning a reading light 82 and/or nightlight on, etc.), closing window blinds or shutters, adjusting a temperature within the environment E, playing audio 84 (e.g., music, audiobooks, sounds conducive to rest and/or sleep, subliminal sessions to be played during sleep, white noise, etc.), initiating an alarm system of a building or unit in which the smart bed 10 is located, determining and adjusting, as necessary, the status of any of various systems and/or devices (heating/air conditioning, lighting, media, appliances, garage doors, etc.) of the building or unit where the smart bed 10 is located, and the like.

Although this disclosure provides many specifics, these should not be construed as limiting the scope of any of the claims that follow, but merely as providing illustrations of some embodiments of elements and features of the disclosed subject matter. Other embodiments of the disclosed subject matter, and of their elements and features, may be devised which do not depart from the spirit or scope of any of the claims. Features from different embodiments may be employed in combination. Accordingly, the scope of each claim is limited only by its plain language and the legal equivalents thereto.

What is claimed:

1. A smart bed, comprising:

a mattress including a sleep surface;

at least one sensor associated with the sleep surface; and a processor in communication with the at least one sensor and programmed to:

detect a presence of at least one individual at or near an edge of the sleep surface of the mattress based on a first signal from a proximity sensor at or near the edge of the mattress;

determine a location of the at least one individual on the sleep surface based on a second signal from a pressure sensor positioned toward a central portion of the mattress a distance from the edge of the mattress;

determine the at least one individual has assumed a sleeping position based on a sequence of events, the sequence of events comprising at least the detection of the presence of the at least one individual at or near the edge of the sleep surface and the determination of the location of the at least individual on the sleep surface based on the second signal from the pressure sensor positioned toward the central portion of the mattress; and initiate at least one function of the smart bed based on the determination that the at least one individual has assumed the sleeping position.

2. The smart bed of claim 1, wherein the processor is further programmed to: determine an orientation of the at least one individual on the sleep surface.

3. The smart bed of claim 2, wherein the processor is programmed to determine whether the at least one individual is in a sitting position on the sleep surface or in a sleeping position on the sleep surface.

4. The smart bed of claim 2, wherein the processor is programmed to determine an orientation of the at least one individual across at least a portion of the sleep surface.

5. The smart bed of claim 1, wherein the processor is further programmed to:

identify the at least one individual present at or near the edge of the sleep surface and initiate the at least one function of the smart bed in a manner that corresponds to an identity of the at least one individual present at or near the edge of the sleep surface.

6. The smart bed of claim 1, further comprising:

a transceiver in communication with the processor.

7. The smart bed of claim 6, wherein the transceiver enables the processor to communicate with a processor of a portable electronic device.

8. The smart bed of claim 7, wherein the processor of the smart bed is further programmed to:

wake the portable electronic device as the processor detects the presence of the at least one individual at or near the edge of the sleep surface; and cause the processor of the portable electronic device to initiate execution of a smart bed control app.

9. The smart bed of claim 7, wherein a smart bed control app on the portable electronic device initiates communication between the processor of the portable electronic device and the processor of the smart bed.

10. The smart bed of claim 9, wherein the smart bed control app enables the at least one individual to use the portable electronic device to control operation of the smart bed.

11. The smart bed of claim 1, wherein the at least one function comprises a temperature of at least a portion of the sleep surface, ventilation of at least a portion of the sleep surface, a firmness of at least a portion of the mattress, an anti-snore feature of the smart bed, an orientation of at least a portion of the mattress, and lighting.

12. A method of using a smart bed, comprising:

detecting a presence of an individual at or near an edge of a sleep surface of a mattress of the smart bed based on a first signal from a proximity sensor at or near the edge of the mattress;

determining a location of the individual on the sleep surface based on a second signal from a pressure sensor positioned toward a central portion of the mattress a distance from the edge of the mattress;

determining a user has assumed a sleeping position based on a sequence of events, the sequence of events comprising at least the detection of the presence of the individual at or near the edge of the sleep surface and the determination of the location of the individual on the sleep surface based on the second signal from the pressure sensor positioned toward the central portion of the mattress; and initiating at least one function of the smart bed based on the determination that the individual has assumed the sleeping position.

13. The method of claim 12, further comprising:

determining an orientation of the individual on the sleep surface.

14. The method of claim 13, wherein determining the orientation of the individual on the sleep surface comprises determining whether the individual is in a sitting position on the sleep surface or in a sleeping position on the sleep surface.

15. The method of claim 13, wherein determining the orientation of the individual on the sleep surface comprises determining an orientation of the individual across at least a portion of the sleep surface.

16. The method of claim 12, further comprising:

identifying the individual present at or near the edge of the sleep surface, the initiating the at least one function comprising initiating at least one function in a manner that corresponds to an identity of the individual present at or near the edge of the sleep surface.

17. The method of claim 12, further comprising:

establishing communication between a processor of the smart bed and a portable electronic device.

18. The method of claim 17, further comprising:

identifying the individual present at or near the edge of the sleep surface, the establishing communication comprising establishing communication between the processor of the smart bed and the portable electronic device of the individual present at or near the edge of the sleep surface.

19. The method of claim 17, wherein establishing communication occurs automatically upon detecting the presence of the individual at or near the edge of the sleep surface.

20. The method of claim 19, wherein establishing communication occurs automatically upon detecting the individual in the sleeping position on the sleep surface.

21. The method of claim 12, wherein initiating the at least one function comprises heating and/or cooling the sleep surface to a pre-set temperature, ventilating at least a portion of the sleep surface, providing the mattress with a pre-set firmness, turning on an anti-snore feature of the smart bed, adjusting an orientation of at least a portion of the mattress, and turning on and/or off lighting features.

* * * * *